Figure 1:
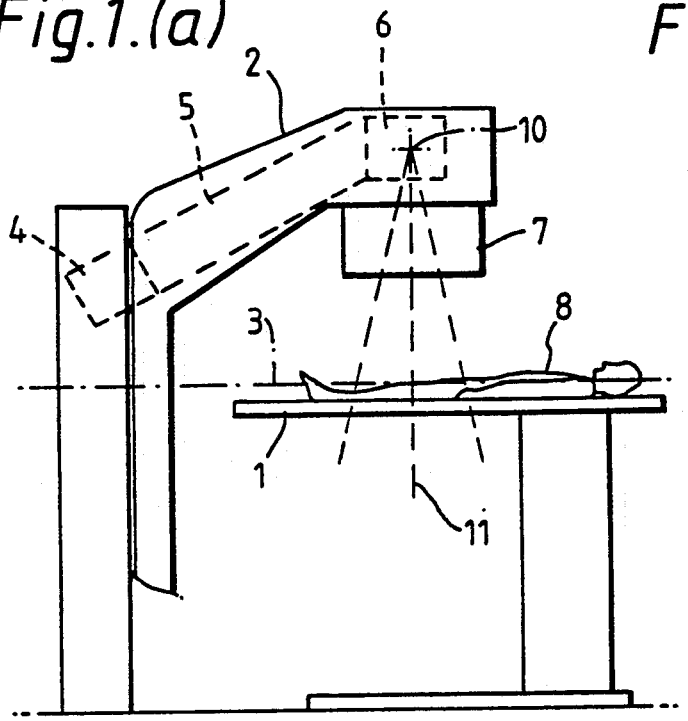
Figure 1:
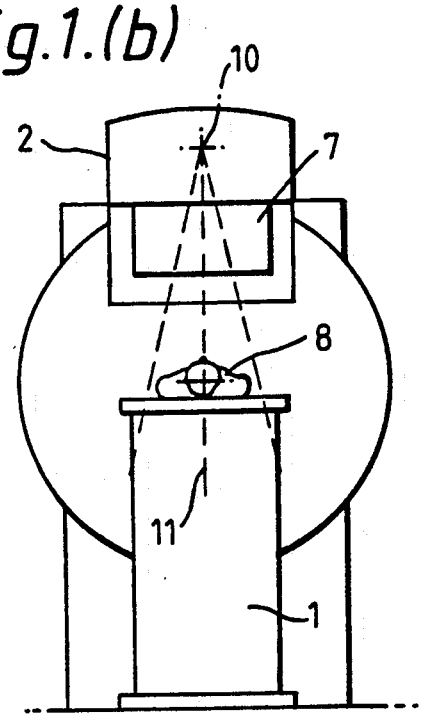

United States Patent [19]
Span et al.

[11] Patent Number: 5,012,506
[45] Date of Patent: Apr. 30, 1991

[54] MULTILEAF COLLIMATOR

[75] Inventors: Francis J. Span, Eindhoven, Netherlands; Brian S. Driver, Langley Green, Great Britain

[73] Assignee: U.S. Philips Corporation, New York, N.Y.

[21] Appl. No.: 255,073

[22] Filed: Oct. 7, 1988

[30] Foreign Application Priority Data

Oct. 28, 1987 [GB] United Kingdom ............... 8925254

[51] Int. Cl.$^5$ ........................................... G21K 1/02
[52] U.S. Cl. ................................... 378/152; 378/150; 378/157; 250/505.1
[58] Field of Search .................... 378/150–152, 378/153, 147; 250/505.1

[56] References Cited

U.S. PATENT DOCUMENTS

| | | | |
|---|---|---|---|
| 4,463,266 | 7/1984 | Brahme | 378/150 |
| 4,464,778 | 8/1984 | Goldmann | 378/151 |
| 4,534,052 | 8/1985 | Milcamps | 378/152 |
| 4,672,212 | 6/1987 | Brahme | 378/150 |
| 4,672,652 | 6/1987 | Huttenranch et al. | 378/152 |
| 4,739,173 | 4/1988 | Blosser et al. | 378/152 |
| 4,754,147 | 6/1988 | Maughan et al. | 378/152 |
| 4,766,603 | 8/1988 | Okabe et al. | 378/152 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |

Primary Examiner—Carolyn E. Fields
Assistant Examiner—David P. Porta
Attorney, Agent, or Firm—Paul R. Miller

[57] ABSTRACT

A collimator is described for a shielded effective point source of penetrating radiation, e.g. a radiotherapy machine which includes, after a primary collimator 16, a succession of a multileaf collimator 17, and a first and a second pair of independently adjustable block diaphragm leaves 30, 31, and 35, 36 at right angles to each other. By using rectilinear displacement of the multileaf collimator leaves 18 and the block diaphragm leaves 30, 31, a compact arrangement can be provided which fits into a standard RT collimator head. By curving the inner edges of the leaves to be tangential to the boundary ray an optimally reduced penumbra can be achieved. The block diaphragms enable the radiation leakage found in prior multileaf collimators to be minimized for small and off center irradiation patterns.

13 Claims, 5 Drawing Sheets

MULTILEAF COLLIMATOR

The invention relates to a collimator for a beam of high energy radiation which is emitted from a substantially point source of radiation, including a multileaf collimator assembly comprising a plurality of adjacent pairs of opposed and in cross-section wedge-shaped leaves, wherein adjacent leaves are arranged side by side to form a fan-shaped configuration converging substantially towards an apex at the effective point location of the radiation source, each wedge shaped leaf being mounted for translational displacement in a direction transverse to the radiation beam, on a support structure such that the leaves of each pair are capable of a displacement independently towards and away from one another, bearing means provided between each leaf and the support structure, motive means for displacing each leaf independently of one another, and readout means to determine the position of the leaves. The invention further relates to a source of penetrating radiation formed by high-energy photons of x-radiation or gamma-radiation or high energy particles such as electrons or protons, provided with a collimator of the kind specified. One use for such a source is for irradiation therapy in the treatment of malignancy.

One form of multileaf collimator of the kind specified is disclosed in European Patent Application A-O-193,590. The multileaf collimator described therein is shown as a continuation of a conventional collimator head and the structure formed thereby adds a considerably to the mass of the treatment head and considerably extends the head in the direction of the patient and increases the size of the beam outlet aperture. This means that it is not possible to use standard auxiliary equipment normally used in conjunction with an irradiation therapy source, such as standard electron applicators or pointers and there would, in general, be insufficient room between the source and the patient to accommodate a blocking ray if required.

It is an object of the invention to provide an improved collimator of the kind specified and a source including the collimator that can reduce the above disadvantages and can provide a multileaf collimator assembly which is no larger than, and can form a direct replacement for a conventional block diaphragm assembly, thus permitting the use of standard attachments such as electron applicators and pointers, and the use of a block tray if required.

According to the invention, this object has been realised in a collimator of the kind specified, characterised in that there is provided in succession along the path of radiation from the source, the multileaf collimator assembly, a first pair of opposed block diaphragm leaves mounted on a support structure for independent translational displacement towards and away from one another in a direction transverse to that of the path of radiation from the source, and a second pair of opposed block diaphragm leaves mounted on a support structure for independent translational displacement towards and away from one another in a direction transverse to the path of radiation from the source and at right angles to the direction of displacement of the first pair of opposed block diaphragm leaves.

The translational displacement of each leaf on the multileaf collimator assembly can be arranged to take place along a rectilinear path perpendicular to the central axis of the radiation beam, and the inner end surface of each leaf can be curved in the radiation beam direction so that it is tangential to the adjacent beam boundary for all displacement positions of the leaf. In this way the penumbra can be reduced to an optimal degree over the adjustment range. The first pair of opposed block diaphragm leaves can be translated in a similar manner in a direction that can be parallel to that of the leaves of the assembly and their inner ends can be similarly curved optimally to reduce penumbra and to provide a compact assembly. The second pair of opposed block diaphragms can be provided with planar inner ends, and can be rotated during translational displacement to maintain the end surfaces parallel to the beam boundary.

The compact arrangement that can be achieved by a collimator in accordance with the invention can be contained within a conventional radiotherapy collimator head enabling standard auxiliary equipment such as pointer and electron applicators to be mounted thereon in conventional manner. Because the normal clearance is thereby maintained between the collimator head and the patient, a blocking tray can be used if necessary. A collimator arrangement in accordance with the invention can provide the facilities of a multileaf collimator with a significant saving in cost and weight over that hitherto proposed. Thus the weight of a collimator in accordance with the invention can be only slightly greater than that of a standard collimator head provided only with blocking diaphragms. Furthermore, a collimator in accordance with the invention can provide a low level of background radiation outside the frame defined by the first and second pairs of block diaphragm leaves, which is equivalent to that for a standard collimator head, while the leakage radiation of a prior multileaf collimator can be significantly greater in practice.

Figure 4:
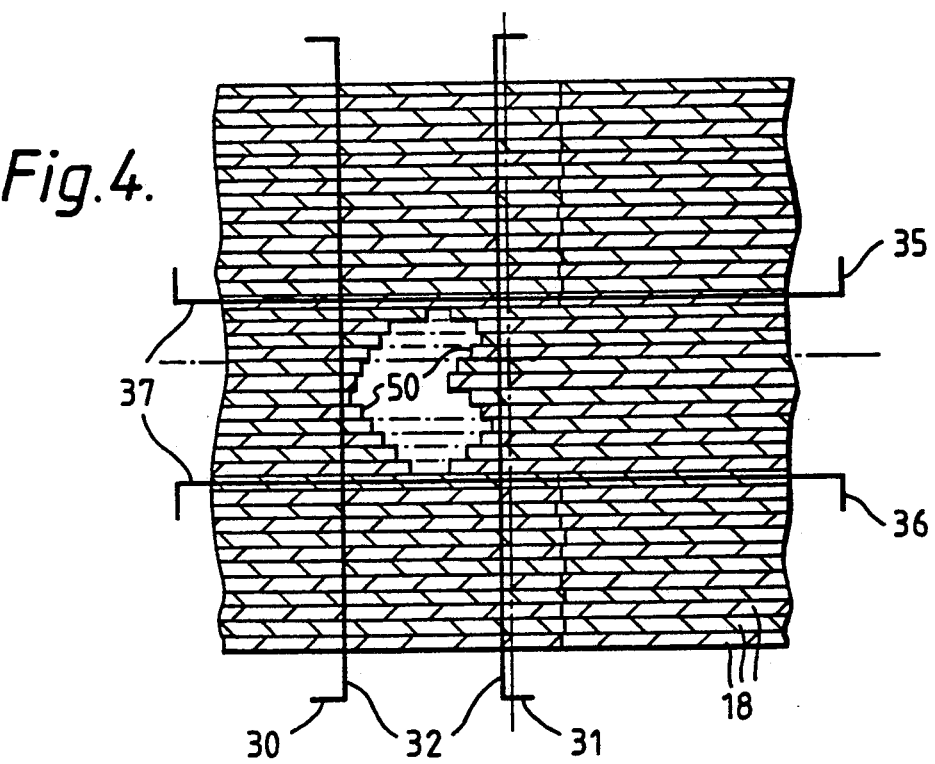
Figure 2:
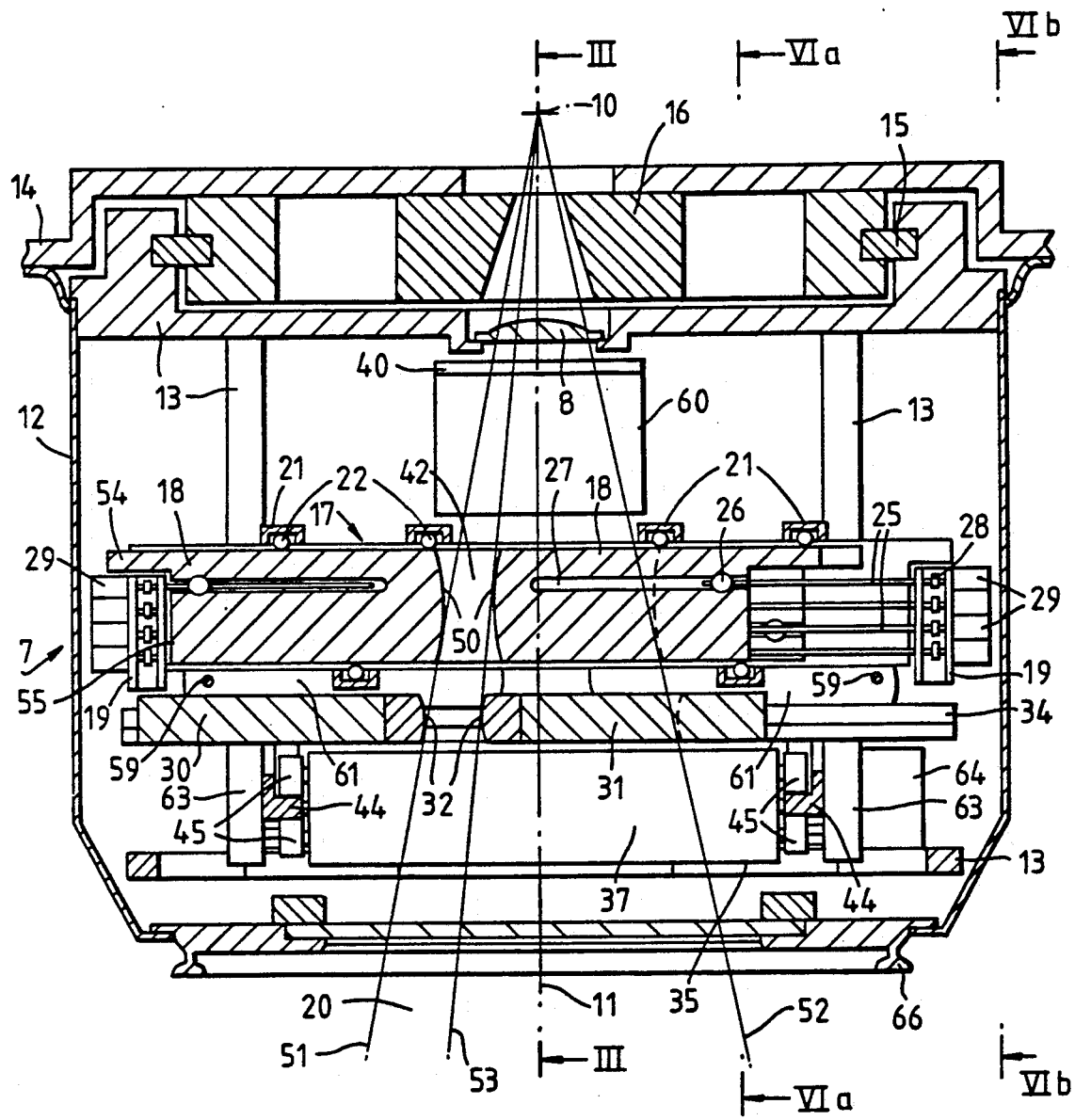
Figure 3:
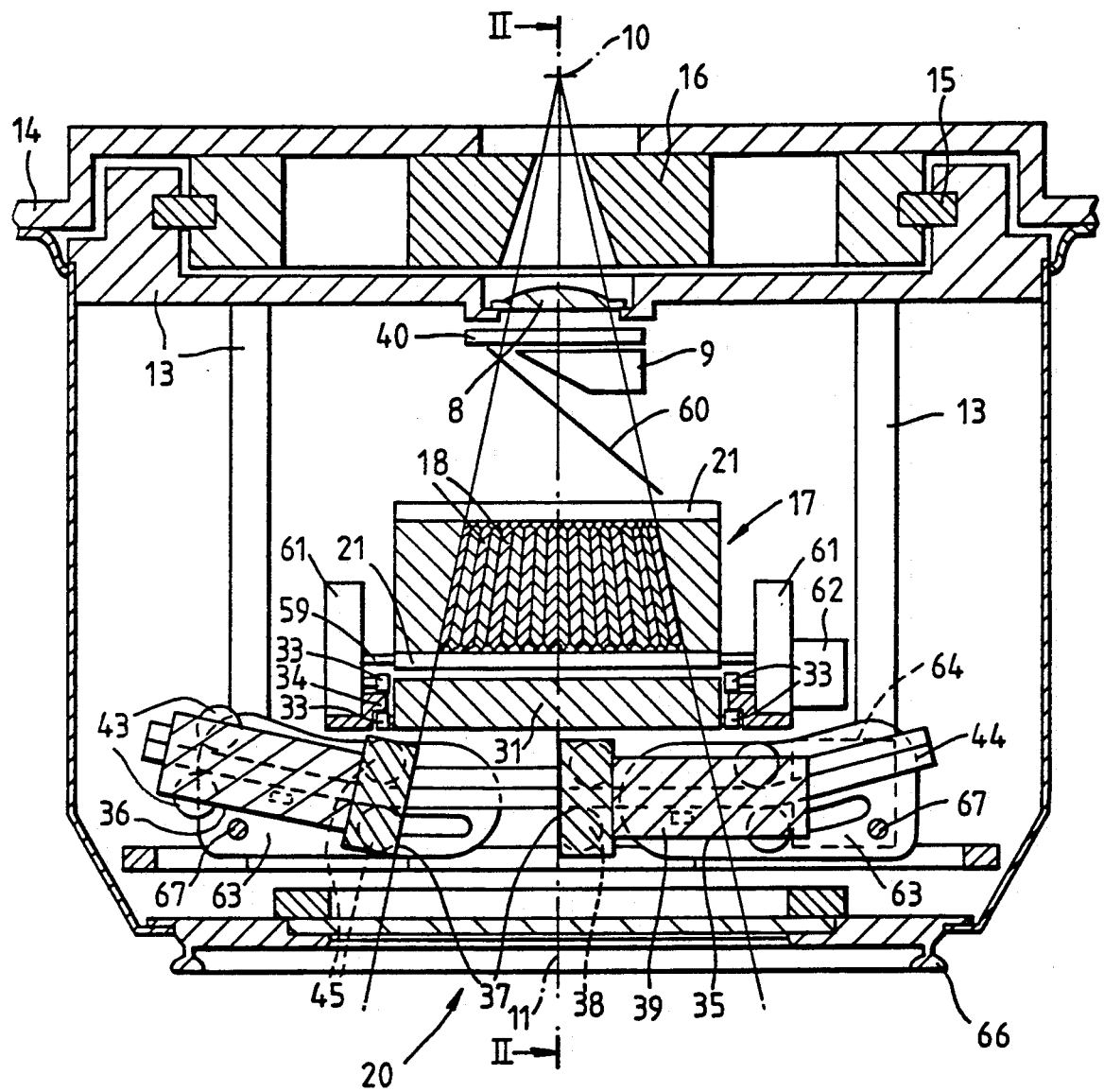
Figure 5:
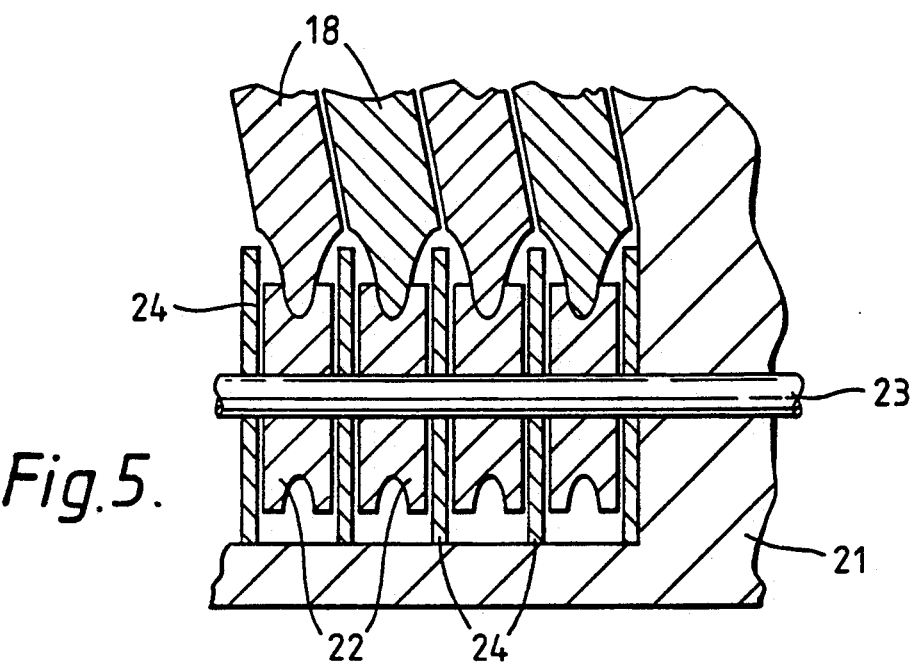
Figure 6:
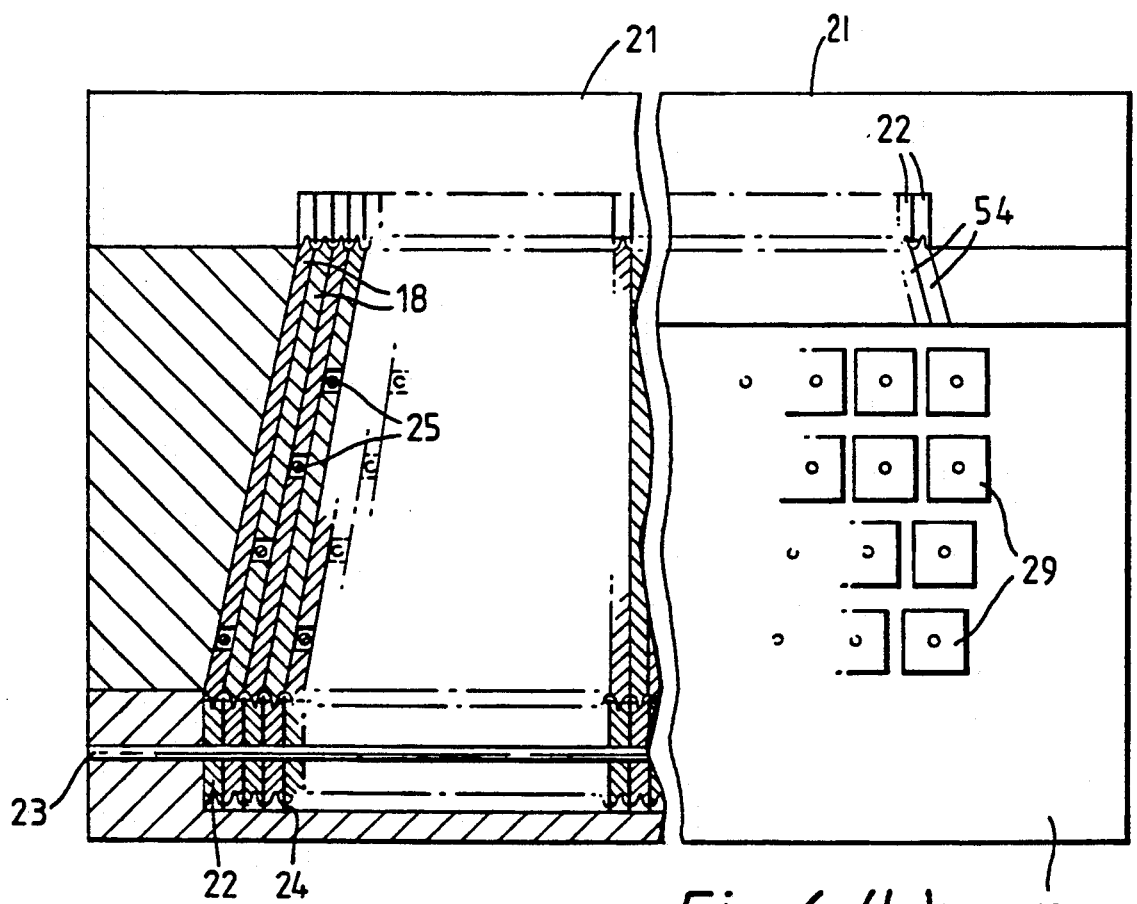
Figure 7:
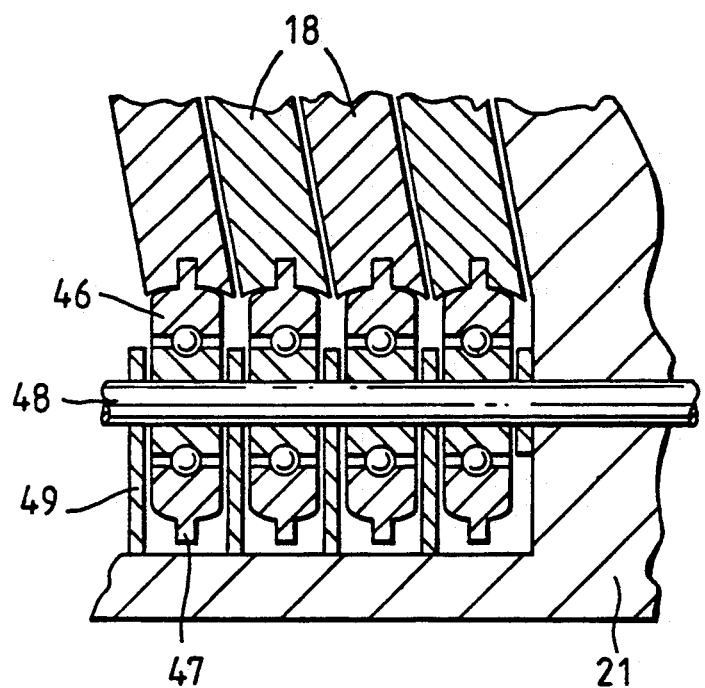

An embodiment of the invention will be described by way of example, with reference to the accompanying schematic drawings, of which:

FIGS. 1(a) and (b) are elevations taken at right angles to one another, illustrating in outline radiotherapy apparatus including a collimating arrangement in accordance with the invention, FIGS. 2 and 3 are orthogonal axial sections of a collimator head in accordance with the invention, taken on the central axis of the irradiation beam, FIG. 4 is a diagram illustrating the irradiation field generated by the collimator, FIG. 5 is an enlarged detail illustrating the bearing support for the multileaf collimator leaves, FIGS. 6(a) and (b) illustrates in transverse section and in end view, respectively, the multileaf collimator assembly, and FIG. 7 is an enlarged detail illustrating an alternative bearing support for the multileaf collimator leaves.

FIGS. 1(a) and (b) diagrammatically illustrate radiotherapy apparatus for irradiating a predetermined region of a patient 8 with a beam of high energy radiation such as electrons or x-rays. The patient 8 is supported on an adjustable table 1. A gantry 2, rotatable through substantially 360 degrees about a horizontal axis 3, supports an electron source 4, a linear accelerator 5 which accelerates the electrons to a selectable energy typically in the range 4–25 MEV, a beam deflection system 6 which deflects the electrons through an angle greater than 90 degrees so that the beam is directed normally towards the axis 3, and a head 7 which includes means 5 for providing the radiotherapy beam with the desired characteristics and which includes a collimator in accordance with the invention. The radiotherapy beam may be the electron beam produced by the linear accelerator or it may be a beam of high-energy X-rays produced by causing the electron beam, after deflection at 6, to strike a suitable x-ray target. The linear accelerator 5 and the beam deflection system 6 are further arranged to bring the electron beam substantially to a point focus 10 which forms the effective point source of the radiation beam emitted by the head 7, whether it be a high energy electron beam, or a high energy x-ray beam which will be generated when an x-ray target is located at the point 10.

The normal radial distance from the source 10 to the horizontal axis 3, i.e. to the isocenter, is 100 cms.

FIGS. 2 and 3 are schematic representations of axial sections of the head 7 taken through the central axis 11 of the irradiating beam in directions at right angles to one another. The head 7, whose purpose, inter alia, is to house collimator means for restricting the cross-section of the irradiating therapy beam in a predetermined and adjustable manner, is provided with a protective outer casing 12 and a supporting structure 13 which is mounted on a supporting gantry arm 14 by means of a supporting bearing 15. Also supported by the gantry arm 14 is a heavy metal primary collimator 16 suitably of tungsten or lead, which is located in the path of radiation from the source point 10. The collimator 16 is provided with a truncated conical aperture whose apex is located at the source point 10 and whose angle of flair is that subtended at the source 10 by the diagonal of the maximum beam cross-section to be provided, which is normally square. Beyond the heavy metal collimator 16 there are provided a conventional flattening filter 8 and an internal wedge filter 9. An ionisation chamber 40 is also conventionally provided to measure and monitor the intensity of the irradiation beam.

A multileaf collimator assembly 17 is provided comprising a plurality of adjacent pairs of opposed heavy metal leaves 18 suitably of tungsten. Each leaf 18 is of wedge shaped cross section and is arranged side by side with the corresponding leaf of the next pair so as to form a fan-shaped configuration converging substantially towards an apex at the effective point location 10 of the radiation source. This can be regarded as focussing the collimator leaves 18 at the source 10, and means that each leaf will cast a full shadow in the beam with minimal sideways penumbra. Each wedge shaped leaf 18 is mounted for translational displacement in a direction transverse to the radiation beam 20, on a support structure 21 arranged so that the leaves 18 of each pair are capable of displacement independently towards and away from one another so that the width of the gap 42 between the inner ends of a corresponding pair of leaves 18 can be adjusted in magnitude and in position. This enables the emitted irradiation field from the head 7 to be defined arbitrarily in rectangular elemental strips whose angular width is determined by the wedge thickness of the leaves. This is illustrated in FIG. 4 by the clear raster area, the shadow cast by the opposing pairs of leaves being shaded.

In accordance with the invention there is provided in succession along the path of radiation from the source 10, after the initial limitation of the beam by the primary collimator 16, the multileaf collimator assembly 17, a first pair of opposed block diaphragm leaves 30, 31, mounted for independent translational displacement towards and away from one another in a direction transverse to that of the path of radiation from the source 10, and a second pair of opposed block diaphragm leaves 35, 36, mounted for independent translational displacement towards and away from one another in a direction transverse to the path of radiation from the source 10 and at right angles to the direction of displacement of the first pair of opposed block diaphragm leaves 30, 31. Thus the multileaf collimator assembly is located significantly closer to the radiation source than in the case of the arrangement disclosed in the aforementioned European Patent Application No. 193,509, which means that smaller and thinner collimator leaves can be employed to provide the same angular size of radiation shadow element at the isocenter i.e. the location of the patient. This results in a considerable saving both in the weight and the cost of the tungsten leaves required to provide a controllable outline for the irradiation area.

In order to provide as compact a multileaf collimator assembly 17 as possible, each leaf 18 of the assembly 18 is arranged to be independently adjustably displaceable along a rectilinear path perpendicular to the central axis 11 of the irradiation beam. Each leaf 18 is supported at the edges by an arrangement of three grooved rollers 22, two spaced along one edge in the present example the upper edge, and one placed intermediately in contact with the other e.g. lower edge, so that the leaf is firmly located in a linearly displaceable manner for all variations in the attitude of the head 7. It will be understood that the gantry 2 can be rotated through about 360 degrees about the horizontal axis 3, and the head 7 can be rotated about the ray axis 11 by means of the supporting bearing 15 through about 200 degrees or more. Referring to FIG. 5, the rollers 22 are free to pivot about a shaft 23 attached at the ends to the hollow open sided supporting beam 21. However, because of the weight of each leaf 18 which is about 1 Kg, and the need to support the 40 leaves which make up each side of the multileaf collimator assembly, the weight of each leaf is carried by respective disc washers 24 which are arranged on each side of each grooved roller 22 and which are of a size to contact at least the inside face of the beam 21 facing the edge of the leaf 18, so as to communicate the supporting force directly to the beam 21 which is firmly connected to and supported by the supporting frame 13.

Each leaf is displaced and located in the direction of displacement by means of a lead screw (threaded drive rod) 25 one end of which engages a nut 26 in the form of a cylinder with a threaded diametrically arranged aperture and which is retained in a cylindrical aperture formed in the leaf 18. The leaf 18 is also provided with a slot 27 to accommodate the lead screw 25 as the leaf is displaced. The other end of the lead screw 25 is connected via a flexible coupling 28 to the output shaft of a reduction gearbox forming part of an electrical drive motor 29 rigidly mounted on a panel 19 which is firmly connected to and supported by the supporting frame 13. The electric motors 29 are controlled via conventional control means (not shown).

FIG. 2 illustrates the left hand leaf 18 in the maximum retracted position enabling the outermost boundary ray 51 to pass. The right hand leaf 18 is shown in its fully inserted position which in the present example is half way across the left hand half of the maximum irradiation field. This range of displacement has been found sufficient for practical requirements. It will be noted that the upper edge 54 of the leaf 18 has been extended outwardly beyond the major part of the outer edge 55 and in the withdrawn position extends past the motor board 19. This is necessary in order to maintain supporting contact with the outer upper roller 22 when the blade 18 is fully inserted into the radiation beam.

The penumbra which will occur due to the inner edge 50 of a leaf 18 not being parallel to the boundary ray for some positions of the leaf 18, can be optimised so as to be fairly uniformly minimal with displacement, by curving the inner edge 50 of the leaf 18 in the radiation beam direction so that the adjacent ray boundary 51, 53, for radiation from the source 10 which just grazes the end surface 50 of the leaf 18, is tangential to the curved surface 50 for all displacement positions, i.e. fully withdrawn to fully inserted respectively, of the leaf 18.

In order to control the leaves 18, their individual positions are monitored via a light-reflecting inclined mirror 60 suitably of metal coated "MYLAR" which is transparent to high-energy radiation, by a video camera (not shown) for example in the manner described in EPA 193,509. The aforementioned control unit (not shown) is then used to compare input positioning signals derived from a treatment control unit (computer) with the actual positions monitored via the video camera, and to provide actuating currents to the corresponding drive motors 29 to cause the leaves 18 to take up the required positions.

In order to accommodate the motors 29 side by side in a compact manner, the threaded drive rods 25 for adjacent leaves are staggered across the transverse (vertical in FIG. 2) dimension of the leaves. Since the width of a motor in the present example is about four times the thickness of the wedge shaped leaves 18 at the uppermost point of attachment, the motors are arranged in four rows as illustrated in the right-hand half (6b) of FIG. 6 which represents an outer end-view of the multileaf collimator assembly.

An alternative form of bearing support for the leaves 18 is illustrated in FIG. 7. In this case the supported edge of each leaf 18 is provided with a groove, and each bearing roller 46 is provided with an outer flange 47 which engages and supports the grooved edge of the corresponding leaf 18. The outer flange 47 comprises the outer rotary member of a ball bearing assembly (ball race) the hub of which is mounted on a stationary support shaft 48 which is supported at intervals between each roller by a support member 49 which relays the supporting thrust directly to the hollow open sided supporting beam 21.

A difficulty associated with a multileaf collimator assembly is that due to leakage of radiation between adjacent leaves. In order to minimise penumbra each wedge shaped leaf is ideally "focussed" onto the effective point source 10 of radiation. This means that the boundary ray on either side should be parallel to the surface of the leaf. At the narrower end the leaves in the present example are about 3 mm thick but a small clearance of about 0.1 mm must be allowed to permit adjacent leaves to be moved relative to one another, and this gap can permit a significant amount of radiation to pass. One way of reducing the leakage of energy from this cause is by "defocussing" wedge shaped leaves relative to the point source 10 by inclining the sides sufficiently to the straight-through beam direction so that a straight passage is not possible through the average 0.1 mm gap. If the sides of the leaves are inclined too far the corresponding region of penumbra in the desired shadow cast by the leaf in the irradiation field, will increase and an optimal compromise has to be aimed for, FIG. 6a is a cross section of the multileaf collimator assembly and the central leaves illustrate an alternative solution to the problem of leakage. In this case a corresponding small step is formed in the facing surfaces of adjacent leaves which is such as to block the direct passage of radiation, however, such a step will also give rise to a slight penumbra effect in the desired shadow cast by the leaf.

The adverse effect of radiation leakage by the multileaf collimator assembly can be limited significantly in accordance with the invention, by following the multileaf collimator assembly 17 by a succession of two pairs of independently displaceable block diaphragm leaves 30, 31, and 35, 36, arranged orthogonally to one another. In this way a rectangular blocking frame can be arranged about any irregular irradiation pattern occupying only part of the maximum irradiation field, and which is limited by a multileaf collimator assembly, enabling the background radiation beyond the inner framing boundary to be reduced in a desirable manner. The framing effect of the inner edges 32 and 37 of the diaphragm leaves 30, 31, and 35, 36, respectively, is illustrated in FIG. 4.

In the present embodiment, the direction of translational displacement of the first pair of opposed block diaphragm leaves 30, 31 is parallel to the direction of translational displacement of the leaves 18 of the multileaf collimator assembly 17. In the illustrative example, each of the block diaphragm leaves are mounted on rollers 33 which respectively engage the upper and lower bearing surfaces of a corresponding rectilinear supporting track 34, as illustrated in FIG. 3. Side thrust rollers (not shown) are also provided at each end of each leaf 30, 31, or at intervals along the track 34 to support the gravitational sideways thrust of the leaves 30, 31, as the attitude of the head is varied. As a preferred alternative, each leaf 30, 31 can be mounted at each side on a corresponding linear bearing. Thus a compact arrangement is provided by displacing the leaves 30, 31 along a rectilinear path. The effects of penumbra associated with the inner ends 32 of the leaves 30, 31, are optimally reduced in a manner similar to that of the multileaf collimator leaves 18, by curving the inner end surface 32 of each leaf in the irradiation beam direction so that the adjacent ray boundary for radiation from the source which just grazes the end surface of the leaf, is substantially tangential to the curved end surface 32 for all corresponding displacement positions of the respective leaf 30, 31.

Each leaf 30, 31 is formed of a heavy metal suitably tungsten or, with less expense, the inner end portion can be made of tungsten so that the residual penumbra is reduced as much as possible while the remainder of the leaf can be made of lead retained in a steel spine or framework. Each leaf 30, 31 is driven independently by a corresponding motor and gearbox assembly illustrated by the block 62 which also includes position sensing means such as a potentiometer coupled to the drive shaft. The drive from the gear box is applied to each side of the leaf via a cross coupling shaft 59 to a corresponding bidirectional supporting mechanism such as a heavy duty lead screw and nut or a belt or well-tensioned chain drive with a minimum of free play, schematically represented by the block 61, so that the position of a leaf 30, 31 will remain constant, once set by the motor 62, as the attitude of the head is varied relative to the pull of gravity. The range of displacement of each of the leaves 30, 31 is made the same as that of the leaves 18 for similar reasons of space.

The second pair of opposed block diaphragm leaves 35, 36, which are displaceable orthogonally to the leaves 18, 30 and 31, are each provided with an inner end surface 37 which is planar, and each leaf 35, 36 is mounted so that the translational displacement of each leaf includes a rotation so that the planar end surface 37 thereof is maintained parallel to the adjacent ray boundary for radiation from the source 10 for all corresponding displacement positions of the leaf. In the case of the second pair of leaves 35, 36, it is sufficient to restrict the range of displacement of the inner face of the leaf to half the maximum irradiation field, i.e. from the centerline 11 to the corresponding outer boundary. This is because any desired offset radiation pattern can be provided mainly by the multileaf collimator and rotation of the head 7 about the beam axis 11.

In the illustrative example each of the leaves 35, 36 can be supported on guide rails 44 in a manner similar to that described for the leaves 30, 31 except that in order to provide the rotation required to maintain the inner planar face 37 "focussed" on the source point 10, the outer end of the support rail 44 must be suitably tilted (upwardly in FIGS. 2 and 3) so that a rearward assembly of upper and lower rollers 43 are correspondingly raised above the level of an inner set of rollers 45 as the leaf 35, 36 is displaced from the central (innermost) position. Displacement of the leaves 35, 36 can be effected in a similar manner to that of the leaves 30, 31 on each side by a corresponding bidirectional supporting mechanism, schematically indicated by the block 63 and comprising for example a lead screw and nut mechanism or a belt drive or a well-tensioned chain drive, driven by a motor, gearbox and position sensing assembly 64 in one case via a cross coupling shaft 67. In this case also the inner end portion 38 of each leaf 35, 36 can be made of tungsten to reduce penumbra while the remainder 39 can be made of lead retained in a steel spine or frame.

As a preferable alternative form of support each of the leaves 35, 36 is pivotably carried at each side on the transverse axis through the center of gravity, by a corresponding nut supported on a respective lead-screw. For each leaf 35, 36 a motor synchronously drives the lead screw on each side of the leaf, in one case via a cross coupling shaft, and the tilt adjustment is provided by a roller follower attached to the outer end of the leaf which is guided by a guide rail, slit or groove.

The collimator in accordance with the invention described with reference to FIGS. 2, 3, 5 and 6, forms a compact arrangement which can be housed in a conventional radiotherapy machine head shell 7 provided with a standard connection 66 for radiotherapy attachments such as pointers or electron applicators, and which will maintain the usual clearance between the collimator head 7 and the patient 8 enabling a blocking tray to be employed if required.

Although the invention has been described in terms of a collimator for a radiotherapy machine it is not limited to such an application and can equally well be employed in other fields in which the irradiation beam from a high energy radiation source must be limited in a similar manner, in industrial applications and in non-destructive testing such as radiography.

From reading the present disclosure, other modifications will be apparent to persons skilled in the art. Such modifications may involve other features which are already known in the design, manufacture and use of collimators for high energy radiation sources and in high energy radiation sources including radiotherapy apparatus and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

What is claimed is:

1. A collimator for a beam of penetrating radiation emitted from a substantially point source of radiation, said collimator comprising
   (a) first and second pluralities of adjacent pairs of wedge-shaped leaves, said first and said second pluralities being disposed in opposition, wherein adjacent leaves of each of said first and second pluralities are disposed side-by-side in a fan-shaped configuration, said configuration converging substantially toward an apex at an effective point location of the source of radiation, and wherein each of said wedge-shaped leaves is disposed for translational displacement in a direction transverse to radiation from the source of radiation on a first support structure, said leaves of each pair being independently displaced toward and away from one another,
   (b) bearing means disposed between each leaf and said support structure for bearing said leaf,
   (c) motive means for displacing each leaf independently of one another,
   (d) readout means for determining position of each of said leaves,
   (e) a first pair of opposed block diaphragm leaves disposed in said radiation at a side of said first and second pluralities opposite to said source of radiation, said first pair of opposed block diaphragm leaves being disposed on a second support structure for independent translational displacement toward and away from each other in a first direction transverse to said radiation,
   (f) a second pair of opposed block diaphragm leaves disposed in said radiation at said side of said first and second pluralities opposite to said source of radiation, and second pair of opposed block diaphragm leaves being disposed on a third support structure for independent translational displacement toward and away from each other in a second direction transverse to said radiation, said second direction being at right angles to said first direction, and
   (g) displacement means for moving each of said first pair of opposed block diaphragm leaves and said second pair of opposed block diaphragm leaves respectively toward and away from each other, wherein the inner end surface of one of said first and second pairs of opposed block diaphragm leaves are planar, and wherein said translational displacement of said one of said first and second pairs of opposed block diaphragm leaves includes a rotational displacement so that said planar end surfaces are maintained parallel to beams of said radiation for all displacement positions of said one of said first and second pairs of opposed block diaphragm leaves.

2. A collimator according to claim 1, wherein said translational displacement of each wedge-shaped leaf is along a rectilinear path perpendicular to a central axis of said radiation.

3. A collimator according to claim 2, wherein an inner end surface of each of said wedge-shaped leaves facing said radiation is curved so that beams of said radiation tangentially graze said inner end surface for all displacement positions of said each leaf.

4. A collimator according to claim 3, wherein said translational displacement of one of said first and second pairs of opposed lock diaphragm leaves is parallel to said translational displacement of said each wedge-shaped leaf.

5. A collimator according to claim 4, wherein said translational displacement of other of said first and second pairs of opposed block diaphragm leaves is along a rectilinear path perpendicular to said central axis of said radiation, and wherein an inner end surface of said other of said first and second pairs of opposed block diaphragm leaves is curved so that beams of said radiation tangentially graze said inner diaphragm leaves for all displacement positions of said other pair of opposed block diaphragm leaves.

6. A collimator according to claim 1, wherein an inner end surface of each of said wedge-shaped leaves facing said radiation is curved so that beams of said radiation tangentially graze said inner end surface for all displacement positions of said each leaf.

7. A collimator according to claim 1, wherein said translational displacement of one of said first and second pairs of opposed block diaphragm leaves is parallel to said translational displacement of said each wedge-shaped leaf.

8. A collimator according to claim 1, wherein said translational displacement of other of said first and second pairs of opposed block diaphragm leaves is along a rectilinear path perpendicular to said central axis of said radiation, and wherein an inner end surface of said other of said first and second pairs of opposed block diaphragm leaves is curved so that beams of said radiation tangentially graze said inner diaphragm leaves for all displacement positions of said other pair of opposed block diaphragm leaves.

9. A radiation source for producing a beam of penetrating radiation having an adjustable boundary comprising
   a shielded radiation point type effective source of penetrating radiation, and
   a collimator including
   (a) first and second pluralities of adjacent pairs of wedge-shaped leaves, said first and said second pluralities being disposed in opposition,
   wherein adjacent leaves of each of said first and second pluralities are disposed side-by-side in a fan-shaped configuration, said configuration converging substantially toward an apex at an effective point location of the source of radiation, and
   wherein each of said wedge-shaped leaves is disposed for translational displacement in a direction transverse to radiation from the source of radiation on a first support structure, said leaves of each pair being independently displaced toward and away from one another,
   (b) bearing means disposed between each leaf and said support structure for bearing said leaf,
   (c) motive means for displacing each leaf independently of one another,
   (d) readout means for determining position of each of said leaves,
   (e) a first pair of opposed block diaphragm leaves disposed in said radiation at a side of said first and second pluralities opposite to said source of radiation, said first pair of opposed block diaphragm leaves being disposed on a second support structure for independent translational displacement toward and away from each other in a first direction transverse to said radiation,
   (f) a second pair of opposed block diaphragm leaves disposed in said radiation at said side of said first and second pluralities opposite to said source of radiation, said second pair of opposed block diaphragm leaves being disposed on a third support structure for independent translational displacement toward and away from each other in a second direction transverse to said radiation, said second direction being at right angles to said first direction, and
   (g) displacement means for moving each of said first pair of opposed block diaphragm leaves and said second pair of opposed block diaphragm leaves respectively toward and away from each other,
   wherein the inner end surfaces of one of said first and second pairs of opposed block diaphragm leaves are planar, and wherein said translational displacement of said one of said first and second pairs of opposed block diaphragm leaves includes a rotational displacement so that said planar end surfaces are maintained parallel to beams of said radiation for all displacement positions of said one of said first and second pairs of opposed block diaphragm leaves.

10. A radiation source according to claim 9, wherein said shielded point type effective source includes a linear electron accelerator.

11. A radiation source according to claim 10, wherein said point type effective source is coupled to said collimator by a rotational coupling having a rotation axis passing through said effective point source.

12. A radiation source according to claim 9, wherein said point type effective source is coupled to said collimator by a rotational coupling having a rotation axis passing through said effective point source.

13. A radiotherapy machine comprising
   a radiation source for producing a beam of penetrating radiation having an adjustable boundary, said radiation source including
   a shielded radiation point type effective source of penetrating radiation, and
   a collimator including
   (a) first and second pluralities of adjacent pairs of wedge-shaped leaves, said first and said second pluralities being disposed in opposition,
   wherein adjacent leaves of each of said first and second pluralities are disposed side-by-side in a fan-shaped configuration, said configuration converging substantially toward an apex at an effective point location of the source of radiation, and
   wherein each of said wedge-shaped leaves is disposed for translational displacement in a direction transverse to radiation from the source of radiation on a first support structure, said leaves of each pair being independently displaced toward and away from one another, (b) bearing means disposed between each leaf and said support structure for bearing said leaf, (c) motive means for displacing each leaf independently of one another, (d) readout means for determining position of each of said leaves, (e) a first pair of opposed block diaphragm leaves disposed in said radiation at a side of said first and second pluralities opposite to said source of radiation, said first pair of opposed block diaphragm leaves being disposed on a second support structure for independent translational displacement toward and away from each other in a first direction transverse to said radiation, (f) a second pair of opposed block diaphragm leaves disposed in said radiation at said side of said first and second pluralities opposite to said source of radiation, said second pair of opposed block diaphragm leaves being disposed on a third support structure for independent translational displacement toward and away from each other in a second direction transverse to said radiation, said second direction being at right angles to said first direction, and (g) displacement means for moving each of said first pair of opposed block diaphragm leaves and said second pair of opposed block diaphragm leaves respectively toward and away from each other, wherein the inner end surfaces of one of said first and second pairs of opposed block diaphragm leaves are planar, and wherein said translational displacement of said one of said first and second pairs of opposed block diaphragm leaves includes a rotational displacement so that said planar end surfaces are maintained parallel to beams of said radiation for all displacement positions of said one of said first and second pairs of opposed block diaphragm leaves.

* * * * *